(12) United States Patent
Kink et al.

(10) Patent No.: US 7,970,461 B2
(45) Date of Patent: Jun. 28, 2011

(54) METHOD AND APPARATUS FOR DETERMINING CONDITIONS OF A BIOLOGICAL TISSUE

(76) Inventors: Andres Kink, Harjumaa (EE); Mart Min, Harjumaa (EE); Toomas Parve, Harjumaa (EE); Indrek Ratsep, Harjumaa (EE)

( * ) Notice: Subject to any disclaimer, the term of this patent is extended or adjusted under 35 U.S.C. 154(b) by 0 days.

(21) Appl. No.: 11/156,757

(22) Filed: Jun. 20, 2005

(65) Prior Publication Data
US 2005/0283091 A1    Dec. 22, 2005

Related U.S. Application Data

(60) Provisional application No. 60/580,831, filed on Jun. 18, 2004, provisional application No. 60/581,298, filed on Jun. 18, 2004.

(51) Int. Cl.
*A61B 5/05* (2006.01)
(52) U.S. Cl. .................................................. 600/547
(58) Field of Classification Search .................. 600/547, 600/554
See application file for complete search history.

(56) References Cited

U.S. PATENT DOCUMENTS

| | | | | |
|---|---|---|---|---|
| 3,316,896 A | * | 5/1967 | Thomasset | 600/547 |
| 3,382,428 A | * | 5/1968 | Sherwood et al. | 324/357 |
| 3,696,808 A | * | 10/1972 | Roy et al. | 600/544 |
| 4,844,086 A | * | 7/1989 | Duffy | 600/544 |
| 5,280,429 A | * | 1/1994 | Withers | 378/70 |
| 5,282,840 A | | 2/1994 | Hudrlik | |
| 5,807,272 A | * | 9/1998 | Kun et al. | 600/547 |
| 5,941,820 A | * | 8/1999 | Zimmerman | 600/300 |
| 5,957,861 A | | 9/1999 | Combs et al. | |
| 6,151,523 A | * | 11/2000 | Rosell Ferrer et al. | 600/547 |
| 6,473,640 B1 | * | 10/2002 | Erlebacher | 600/547 |

(Continued)

FOREIGN PATENT DOCUMENTS
RU    2225160    10/2002
(Continued)

OTHER PUBLICATIONS

Kink, Andres et al., "Bioimpedance Based Analysis of Tissue Oedema", Proc. of the XII Internat. Conf. on Electrical Bioimpedance & the V. Conf. on Electrical Impedance Tomography ICEBI/EIT 2004, Jun. 20-24, 2004, vol. 1, pp. 29-32, Gdansk, Poland.

(Continued)

*Primary Examiner* — Max Hindenburg
*Assistant Examiner* — Rene Towa
(74) *Attorney, Agent, or Firm* — Vern Maine & Associates (57) ABSTRACT

In one method, one or more excitation signals with the same or different frequencies are applied to a biological object such as a tissue, simultaneously or consequently. Response signals are then cross-correlated with delayed excitation signals. Cross-correlation products are then auto-correlated. Cross-correlation products correspond to conditions of the tissue and auto-correlation product corresponds to changes in the conditions. Measuring electrical characteristics at low, intermediate and high frequency is also disclosed. At low frequency, the current flows mostly through the extracellular liquid of tissue. At high frequency, the current passes through the cell membranes freely enough to dominate the overall impedance. At both frequencies, the delay is less than 1/30 of the period of the respective signal. The intermediate frequency between the low frequency and the high frequency carries information about quick changes in the condition of the tissue. The delay in one example is from about 1/30 to 1/4 of the period of the intermediate signal.

18 Claims, 5 Drawing Sheets

U.S. PATENT DOCUMENTS

| | | | |
|---|---|---|---|
| 6,496,725 B2* | 12/2002 | Kamada et al. | 600/547 |
| 6,532,384 B1* | 3/2003 | Fukuda | 600/547 |
| 6,760,617 B2* | 7/2004 | Ward et al. | 600/547 |
| 6,970,738 B1* | 11/2005 | Othman et al. | 600/547 |
| 7,122,012 B2* | 10/2006 | Bouton et al. | 600/587 |
| 2001/0051774 A1* | 12/2001 | Littrup et al. | 600/547 |
| 2003/0216661 A1* | 11/2003 | Davies | 600/547 |
| 2004/0172080 A1 | 9/2004 | Stadler et al. | |
| 2005/0090758 A1 | 4/2005 | Parsonnet et al. | |

FOREIGN PATENT DOCUMENTS

| | | |
|---|---|---|
| RU | 2242165 | 12/2004 |
| WO | WO 00/79255 A1 | 12/2000 |
| WO | WO 01/19426 A2 | 3/2001 |
| WO | WO 2004/045406 A1 | 6/2004 |
| WO | WO 2004/050178 A1 | 6/2004 |
| WO | WO 2004/052198 A1 | 6/2004 |

OTHER PUBLICATIONS

Grimnes, Sverre et al., "Bioimpedance and Bioelectricity Basics", 2000, pp. 99-101, 114-118, 188-192, 282-284, Academic Press, San Diego, California.

Thiel, F. et al., "Semiparallel, Multi-Frequency Equipment for Electrical Bio-Impedance Measurements", Proceedings of the XI International Conference on Electrical Bio-Impedance XI ICEBI2001, Jun. 17-21, 2001, pp. 225-228, Oslo, Norway.

Osypka, M. et al., "Parallel Signal Processing and Multi-Electrode Current Feeding in a Multi-Frequency EIT-System", Innov. Tech. Biol. Med., 1994, pp. 57-61, vol. 15, No. 1.

Min, Mart et al., "Electrical Impedance and Cardiac Monitoring Technology, Potential and Application", International Journal of Bioelectromagnetism, 2003, vol. 5, No. 1, pp. 53-56.

Gersing, Eberhard, "Impedance spectroscopy on living tissue for determination of the state of organs", Bioelectrochemistry and Bioenergetics 45, 1998, pp. 145-149, Elsevier Science S.A.

Gheorghiu, Mihaela et al., "On the Quantitative Elevation of the Time Course of Tissue Impedance During Ischemia", Proceedings of the XI International Conference on Electrical Bio-Impedance, XI ICEBI2001, Jun. 17-21, 2001, pp. 49-53, Olso, Norway.

Howie, Michael, et al., "An Evaluation of a New Two-Electrode Myocardial Electrical Impedance Monitor for Detecting Myocardial Ischemia", Anesth Analg, 2001, 92, pp. 12-18, International Anesthesia Research Society.

Min, Mart et al., "Improvement of the vector analyser based on two-phase switching mode synchronous detection", Measurement, 1996, pp. 103-111, vol. 19, No. 2, Elsevier Science Ltd, The Netherlands.

Burdett, Richard, "183: Correlators in Signal Extraction" Handbook of Measuring System Design, 2005, vol. 3, pp. 1217-1219, John Wiley & Sons Ltd, England.

Schafer, M. et al., "Monitoring of Physiological Process in Ischemic Heart Muscle by Using a New Tissue Model for Description of the Passive Electrical Impedance Spectra", Proceedings of the XI International Conference on Electrical Bio-Impedance ICEBI2001, Jun. 17-21, 2001, pp. 55-58, Olso, Norway.

Min, Mart et al., "Lock-in measurement of bio-impedance variations", Measurement 27, 2000, pp. 21-28, Elsevier Science Ltd.

Casas, O. et al., "In Vivo and In Situ Ischemic Tissue Characterization Using Electrical Impedance Spectroscopy", Annals of the New York Academy of Sciences, 1999, vol. 873, pp. 51-58, The New York Academy of Sciences, New York, New York.

Gheorghiu, Mihaela et al., "Quantitative Analysis of Impedance Spectra of Organs during Ischemia", Annals of the New York Academy of Sciences, 1999, vol. 873, pp. 65-71, The New York Academy of Sciences, New York, New York.

Schafer, M. et al., "Dielectric Properties of Skeletal Muscle during Ischemia in the Frequency Range from 50 Hz to 200 MHz", Annals of the New York Academy of Sciences, 1999, vol. 873, pp. 59-64, The New York Academy of Sciences, New York, New York.

\* cited by examiner

METHOD AND APPARATUS FOR DETERMINING CONDITIONS OF A BIOLOGICAL TISSUE

CROSS REFERENCE TO RELATED APPLICATIONS

This application claims the benefit of U.S. provisional patent applications No. 60/581,298 and No. 60/580,831, both filed on Jun. 18, 2004. Both applications are incorporated herein by reference in its entirety for all purposes. U.S. patent application Ser. No. 10/537,643, filed Jun. 6, 2005 is incorporated herein by reference in its entirety.

TECHNICAL FIELD

The invention relates to the field of medical diagnostics, namely to determining conditions of an object by measuring its electrical properties, and more particularly, in some embodiments, to the measurement of the electrical bio-impedance (EBI) of a bio-object, such as a biological tissue or an organ. In one embodiment the system uses excitation signals having frequencies characteristic to the tissue or the organ, and measuring response signal correlation and subsequent processing of results according to auto-correlation principles. More specifically, in other embodiments, to a method and device for monitoring edema using the EBI measurement at only a few characteristic frequencies.

BACKGROUND OF THE INVENTION

One of the fields of application of the invention is related to the measurement of EBI in portable, wearable, and/or implantable medical devices and apparatuses for determining the conditions of organs and tissues, especially of transplantable and/or transplanted organs and tissues.
Biomedical Background Tissue edema is, in general, a pathological change in liquid amount and balance in the tissue. Depending on their initial causes, the edemas are found to be of three types: cellular, extracellular (interstitial) and combined (see A. Kink, M. Min, T. Parve, I. Rätsep. Bioimpedance based analysis of tissue oedema. In: Proc. of the XII Internat. Conf. on Electrical Bioimpedance & the V Conf. on Electrical Impedance Tomography ICEBI/EIT 2004, Jun. 20-24, 2004, Gdansk, Poland, Vol. 1, pp. 29-32, incorporated herein by reference).

The cellular edema, which is known also as the ischemic or cytotoxic edema, occurs either through intracellular hyperosmolarity or through extracellular hypotonicity as a result of occlusion of the oxygen rich blood inflow or the arterial supply of tissue. The cellular edema results in swelling of cells due to sucking in the fluid from extracellular space.

The extracellular edema, known also as interstitial edema, is a result of buildup of fluids in extracellular space of the tissue (parenchyma). There are two ways for genesis of the extracellular edema:

a) the hydrostatic extracellular edema develops through increased ultrafiltration (leakage through the walls of capillars) or due to decreased reabsorption (inhibition of the venous outflow), b) the oncotical extracellular edema is caused by shortage of proteins (swelling from starvation).

The combined edema includes both types of edema, cellular and extracellular, in some proportion. Both types of edema can be present together from the beginning of edema processes, but they can also develop successively depending on the initial cause (i.e., either the occlusion of arterial supply or venous outflow). As a rule, however, one type of edema causes the other to develop and vice versa in a mutually progressive way (called compartment syndrome).

Independently of the type or cause of the edema, the amount and balance of liquid in the tissue changes during edema which in turn can be monitored as changes in bio-impedance of the tissue (see S. Grimnes and Ø. G. Martinsen, *Bioimpedance and Bioelectricity Basics*, Academic Press, San Diego, 2000).

A developing cellular (ischemic) edema increases EBI of the tissue at lower frequencies, but the EBI decreases again after the blood circulation is restored. At higher frequencies the variations of impedance can be negligible. A permanently progressive edema can quickly lead to complete damage of the tissue through cell destruction. At this stage of edema, the impedance of the tissue at low frequencies decreases rapidly.
Engineering Background PCT application WO 01/19426 "Implantable Device and Method for Long-Term Detection and Monitoring of Congestive Heart Failure" describes a measuring device, which is mounted into a pacemaker. Such device is used for observing complications developing in the cardiac blood vessel system and in the blood circulation in lungs. The method is based on directing various types of current/voltage excitation signals (rectangular waveform signal, sine wave signal, pulse signal, signal with varying frequency) through a bio-object and measuring the inphase and quadrature components of the electrical response to the excitation signal. The device measures variations in the impedance of the cardiac blood vessel system and of the blood circulation in lungs via measuring a current flow through the object, a voltage drop forming on it and a phase shift between the excitation and response signals. The described device enables this device to diagnose the interstitial edema in lungs.

The electrical bio-impedance (EBI) can give valuable information about both current condition of the tissue and changes in its conditions over a period of time.

PCT application WO 00/79255 "A method and device for Measuring Tissue Edema" suggests that presence of edema in a tissue can be diagnosed by measuring and comparing bio-electrical impedance of the tissue at a single low-frequency voltage at=two anatomical regions of a subject, one of the regions being unaffected by edema. For example, presence of edema in patient's right arm is determined by measuring the electric bio-impedance of the right arm and comparing it with the bio-impedance of the left arm. The frequency of the voltage according to one described method is 5 to 20 kHz, and preferably 10 kHz.

From the results of electrical impedance spectroscopy (see F. Thiel, G. Hahn, E. Gersing, T. Dudykevych, C. Hartung and G. Hellige, Semiparallel, multi-frequency equipment for electrical bio-impedance measurement, in *Proc. of the XI Int. Conf. Electrical Bio-Impedance* ICEBI2001, Jun. 17-21, 2001, Oslo, Norway, pp. 225-228; M. Osypka and E. Gersing. Parallel signal processing and multi-frequency EIT system, in *Innov. Tech. Biol. Med.*, vol. 15, 1994, Special issue No. 1, pp. 56-61; M. Min, S. Ollmar, and E. Gersing, Electrical Impedance and Cardiac Monitoring—Technology, Potential and Applications, —*Internat. Journal of Bioelectromagnetism*, Vol. 5, 2003, No. 1, pp. 53-56; E. Gersing. Impedance spectroscopy on living tissue for determination of the state of organs, —*Biochemistry and Bioenergetics*, 45 (1998), pp. 145-149) it is possible to determine characteristic frequencies for a particular type of tissue, at which the analysis of electrical bio-impedance (EBI) can give the most valuable information about the tissue. At these frequencies the sharpest changes take place when the tissue is going through the different stages of edema. Selection of frequencies depends on the type of edema (cellular, interstitial, combined) and structure of tissue (myocardium, liver, brain, etc). For example, the study of canine liver (M. Gheorghiu, E. Gersing, E. Gheorghiu, On the quantitative evaluation of the time course of tissue impedance during ischemia, in *Proc. of the XI Int. Conf. Electrical Bio-Impedance ICEBI*2001, Jun. 17-21, 2001, Oslo, Norway, pp. 49-53) by wide range impedance spectroscopy showed that the low frequency should be chosen below 1 kHz, and the high frequency should be chosen above 10 kHz. For monitoring a muscle flap, the low frequency was chosen 170 Hz, intermediate frequency 10 kHz and high frequency 150 kHz (see A. Kink, et al, above).

Impedance spectroscopy gives good results in laboratory conditions (see e.g., E. Gersing. Impedance spectroscopy on living tissue for determination of the state of organs, —*Biochemistry and Bioenergetics,* 45 (1998), pp. 145-149), but cannot be used in wearable and implantable devices.

Theoretically, application of pure sine wave signals is presumed for determination of the complex impedance by its definition. Application of switching mode electronics operating with pulse signals (M. B. Howie, R. Dzonczyk, T. D. Sweeny. An evaluation of a new two-electrode myocardial electrical impedance monitor for detecting myocardial ischemia, *Anesth Analg,* 2001, 92, pp. 12-18) has been used frequently in low power devices, but misleading measurement errors appear due to uncertain impact of higher harmonics present in the pulse signals. For example, application of the simplest rectangular waveform pulses, most suitable for use in CMOS electronics, introduces serious measurement errors (see M. Min, and T. Parve, "Improvement of the vector analyser based on two-phase switching mode synchronous detection", Measurement, Vol. 19 (1996), No. 2, pp. 103-111, incorporated herein by reference). However, these errors can be reduced substantially by methods and techniques described in PCT application PCT/EE03/00006 (published as WO2004/052198 on Jun. 30, 2004, and corresponding U.S. patent application Ser. No. 10/537,643, filed into national phase in the U.S. on Jun. 6, 2005, both applications incorporated herein by reference in their entirety).

In the solution described in the PCT application WO 00/79255 "A method and device for Measuring Tissue Edema" the EBI of the tissue is compared with the EBI of an analogical sample tissue. However, no such sample tissue is generally available, particularly in the case of a transplanted tissue. Furthermore, even if a sample is available on rare occasion, it is complicated to introduce and retain the electrodes in a sample tissue and in a tissue to be monitored identically, and therefore, indeterminacy occurs in comparing results from these tissues.

As wide range impedance spectroscopy is badly suitable for clinical practice, a method of edema monitoring using the EBI measurement at only some characteristic frequencies is taken under discussion, see U.S. Pat. No. 6,532,384 to Fukuda. This invention, however, is based on the simplest electrical model of a tissue, known as Cole-Cole model. In reality, the model of a tissue should be much more complicated. Therefore, Cole-Cole model leads to inaccurate choice of excitation frequencies. Methods based on Cole-Cole model comprise hardly quantifiable measurement errors, specifically when non-sinusoidal excitation signals must be used. Non-sinusoidal, i.e., pulse wave excitation signals are typical, e.g., for implantable devices (see PCT patent applications WO 2004/045406 and WO 2004/050178).

SUMMARY OF THE INVENTIONS

One aspect of the invention is a method for determining a relative amount of intracellular and extracellular liquid (water) based on measurement and analysis of electrical bio-impedance (EBI) or electrical conductivity of the tissue. The alternating current excitation signal (current) is generated into the tissue or organ and a response signal to the excitation current is measured using cross-correlation technique (R. Burdett, Correlators in Signal Extraction. Ch. 183 in P. H. Sydenham and R. Thorn (eds.), *Handbook of Measuring System Design. Vol.* 3. John Wiley & Sons, 2005, pp. 1217-1219). In the cross-correlator, the response signal is multiplied by the delayed reference signal, which is a normalized copy of the excitation signal. The multiplication product is allowed to averaging, which suppresses noise and high frequency components and extract slower components changing according to variations in EBI.

Another aspect of the invention is a system and device for practicing the above methods.

The cross-correlation products allow autocorrelation to compare and follow the changes of parameters over some time interval—adjustable lag interval. The cross-correlation and auto-correlation results are used to calculate required indices for characterization of dynamics of the relative amount of extracellular and intracellular liquid in the biological tissue.

Another aspect of the invention is a method for determining conditions of tissue, corresponding to the relative amount and dynamics of extracellular and intracellular liquid in the biological tissue, more specifically, the dynamics (i.e., stage and progress) of edema. The proposed method for the edema analysis is based on EBI measurement at only few frequencies which are the most informative and characteristic for a particular tissue under study.

Another aspect of the invention is a method for determining conditions of transplanted tissues and organs, including such characteristics as reperfusion level, resuscitation grade, and reviability. Also, conditions of tissues and organs to be transplanted can be determined, namely viability of such tissues and organs.

According to one aspect of the invention, EBI is measured at two frequencies that are chosen so that one of the frequencies is low enough not to let the measurement current pass the cell membranes of the tissue, but to flow mostly through the extracellular liquid of any type of tissue, and particularly, through the gap junctions as galvanic paths of the intracellular liquid in the case of myocardium tissue (M. Schäfer, W. Gross, J. Ackemann, M. Mory, M. M. Gebhard, Monitoring of physiological process in ischemic heart muscle by using a new tissue model for description of the passive electrical impedance spectra, in *Proc. of the XI Int. Conf Electrical Bio-Impedance ICEBI*2001, Jun. 17-21, 2001, Oslo, Norway, pp. 55-58). The delay time for cross-correlation should be short in this case, less than $\frac{1}{30}$ of excitation period. Closing of the gap junction, and corresponding reducing of conductivity at the low frequency and changing of balance between extracellular and intracellular liquid, gives information for early signaling about the myocardium's ischemia.

The other characteristic frequency is chosen high enough so that the current passes through the cell membranes freely enough to allow the intracellular liquid to affect the overall impedance in the amount which can be determined by analysis of the measurement results. In both cases, only the resistive part of the current carries information. At these frequencies, the maximum value of the cross-correlation product must be achieved at the very short delay, less than $\frac{1}{30}$ of the excitation period. To obtain required parameters, the delay is adjustable.

Another aspect of the invention is a method for diagnosing the type of edema (cellular, extracellular, or combined), and for early detecting the smallest changes in the stage of edema. Measuring at one or more intermediate frequency is used for early detecting changes in conditions of the tissue state. In this case, the delay can be adjusted to different values from 1/30 up to 1/4 of the excitation period. Now the delay time and both, the resistive (inphase) and capacitive (quadrature) components of the current carry information about the changes in tissue (see M. Gheorghiu, E. Gersing, E. Gheorghiu, Quantitative analysis of impedance spectra of organs during ischemia, in *Annals of N.Y.A.S.*, vol. 873, 1999, pp. 65-71; A. Kink, M. Min, T. Parve, I. Rätsep, Gdansk, above).

The methods and devices according to the invention are most suitable for determining the stage of edema by measuring its EBI when no sample tissue or organ is available.

The excitation signals can be applied either consecutively, or simultaneously. For the cardiac ischemia monitoring, the fully simultaneous measurements are typically used because the beat-to-beat changes of intracardiac impedance are typically substantially bigger than changes from the starting edema (ischemia).

Another implementation of the invention is placing bio-impedance measurement electrodes (excitation electrodes and response electrodes), during off-pump coronary artery bypass grafting surgeries, using vacuum heart stabilizer. Such electrodes are positioned between the vacuum heart stabilizer and the heart, and are securely fixed when the heart is sucked against the vacuum heart stabilizer, thereby providing good and secure contact between electrodes and myocardial wall of the heart. Using the methods according to present invention allow for such aspects as monitoring signs of ischemic conditions during the surgery and to prevent heart failure (heart attack) during the surgery.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposed, and not to limit the scope of the inventive subject matter.

DETAILED DESCRIPTION OF THE INVENTIONS

In the following discussion, like numbers apply to like parts.

Figure 1:
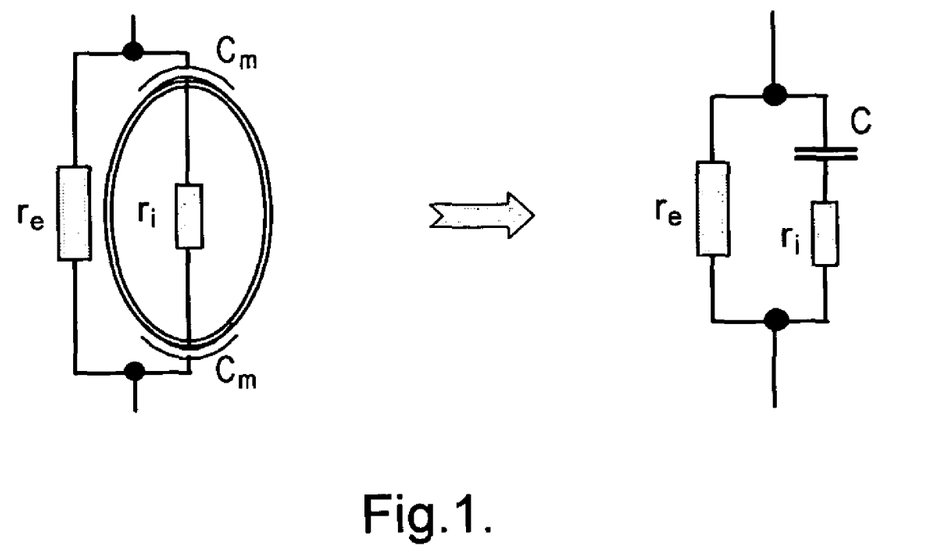
FIG. 1 depicts a simplified electrical equivalent circuit of conductivities of a living biological tissue.

First, we refer to FIG. 1. Method according to one embodiment of the invention is based on the notion that the electric conductance of a tissue $g_L$ at low frequency $f_L$ characterizes the amount of the extracellular liquid in that tissue (see a very much simplified model of a biological living tissue in FIG. 1). If the low frequency $f_L$ is selected sufficiently low (usually, 10 to 1000 Hz), the current does not pass the cellular membranes of the tissue as the capacitive impedance $1/2\pi f_L C_m$, where $C_m$ is capacitance of cell membrane, is substantially bigger than the impedance of extracellular fluid $r_e$. At that low frequency, $g_L=1/r_e$.

On the other hand, if the frequency $f_H$ is selected high enough (usually 10 kHz to 10 MHz), the capacitive impedance $1/2\pi f_H C_m$ of the cellular membrane is not substantial at that frequency (the capacitive impedance must be less than the impedance of intracellular liquid $r_i$). The conductance of the tissue at such frequency is directly dependant on the amount of liquid at a particular volume of the tissue. At that frequency, electric conductance of the tissue $g_H=1/r_e+1/r_i$.

The stage of edema (relative amount of liquid in a unit of volume) is determined as following.

Determining the amount of extracellular liquid from the conductance to a low frequency current;

Determining the total amount of the liquid in a normalized volume of the tissue from the conductance to a high frequency current;

Determining the amount of intracellular liquid as a difference between the total amount of liquid and the amount of extracellular liquid.

In principle, we underline in the invention that the Cole-Cole model with lumped equivalent circuit (U.S. Pat. No. 6,532,384 to Fukuda) and using of complex impedance concept, do not correspond well enough to the real tissue because the tissue is a three-dimensional object and it is not homogenous piece of biomaterial. Bio-objects generally have distributed parameters. The excitation signals can have different waveforms from classical sine wave to short pulses (PCT WO 2004/045406, inventor Parsonnet, corresponds to U.S. Patent Publication No. 2005/090758). It is important to understand that theory of complex variables and notion of complex impedance (real and imaginary parts, and magnitude and phase) presume pure sine waves by the definition.

Instead, we propose to use cross-correlation technique (see R. Burdett, above) with using such a generalized parameters as correlation delay time $\tau_M$, at which the correlation product has the maximal value ($C_{T,\tau_M}$=max). The correlation method corresponds quite well to the real physical situation and any suitable excitation waveform can be used at measurements.

It is characteristic that only the resistive component of the current or the resistive part of the impedance carries information both in the case of low frequency current and high frequency current. The delay between excitation signal and response signal must be small, typically less than 1/30 of the period $T_L=1/f_L$ of the low frequency signal or $T_H=1/f_H$ of the high frequency signal, respectively.

The electric conductance of the tissue at an intermediate frequency $f_M$ is more complex and has both resistive and capacitive components, and the delay between excitation signal and response signal can be up to 1/4 of the period $T_M=1/f_M$ of the intermediate frequency signal, but typically the delay around T/12 gives the maximal cross-correlation product.

Figure 2:
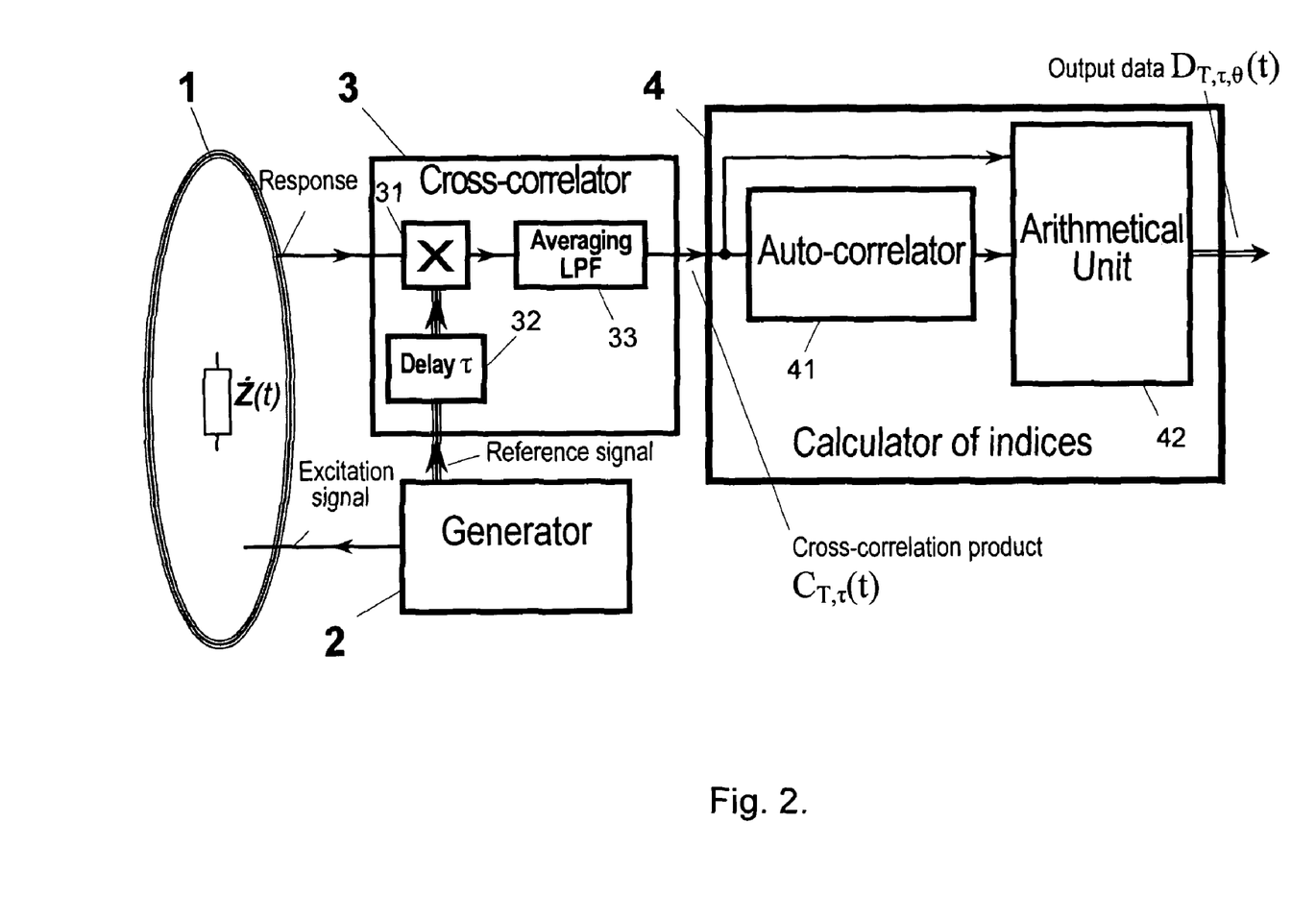
FIG. 2 depicts a structural scheme of a tissue state analyzer according to one embodiment of present invention.

The device in FIG. 2 is designed to practice the above method. A bio-object 1, such as a biological living tissue or an organ, has a complex EBI Ż that is changing over time. An excitation generator 2 provides as an excitation signal (current) to said bio-object, as well as a reference signal to a cross-correlator 3. A response signal from the bio-object is supplied to an input of the cross-correlator and is multiplied with the delayed reference signal. The delay time τ of the reference signal is adjustable. An averaged output signal of the cross-correlator 3 contains the results of signal processing—cross-correlation indices $C_{T,\tau}(t)$ for a frequency of a given excitation signal f=1/T (where T is the period of the excitation signal) and selected delay time τ, whereas the indices are changing in time t with the change of impedance Ż. Cross-correlation indices are then given to an auto-correlator 41, where the cross-correlation indices at one moment of time (first moment) are auto-correlated with the correlation indices calculated for a different moment of time (second moment). The lag interval θ between the first moment of time and the second moment of time is chosen specially for a particular type of tissue and for a particular type of the process monitored. For example, θ can be about 1 minute where the object monitored is transplanted heart, or about 30 minutes where the object is a muscle flap attached to a limb during a reconstructive surgery.

Both static and dynamic edema indices $D_{T,\tau}(\theta)$ and $D_{T,\tau,\theta}(t)$ are subsequently calculated in an arithmetical unit 42 from the results of both auto-correlation and cross-correlation, and can be presented digitally and/or graphically.

Figure 3:
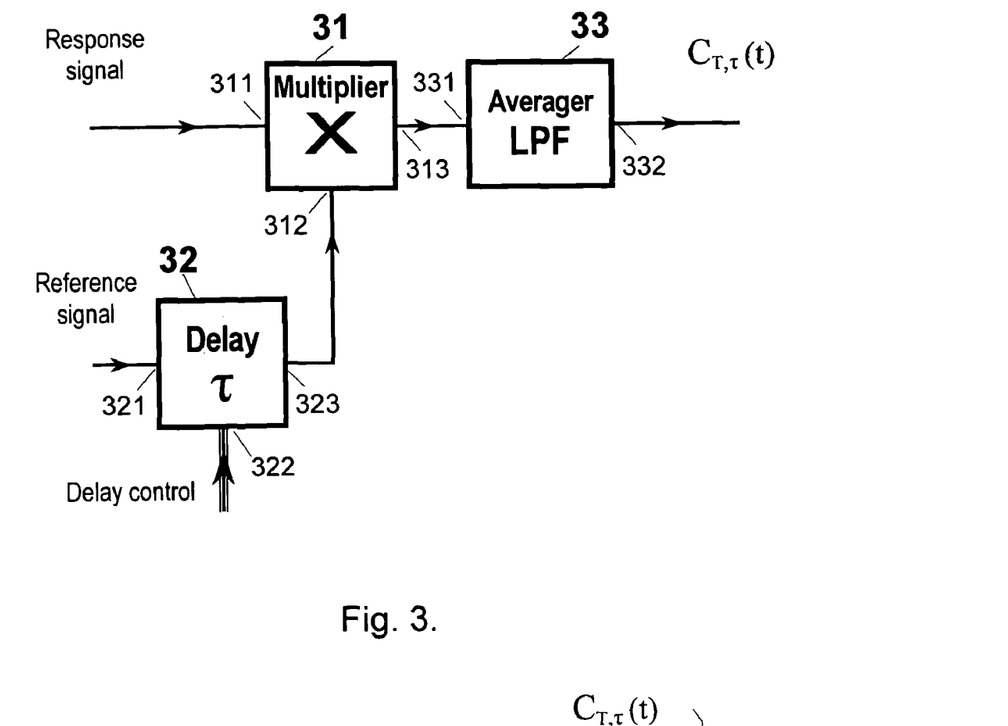
FIG. 3 depicts a cross-correlator, used in the device of FIG. 2 to correlate response and reference signals (delay τ is adjustable) according to one embodiment of present invention.

FIG. 3 describes the operation of the cross-correlator 3 in more details. The response signal from the bio-object 1 is applied to an input 311 of a multiplier 31. A reference signal from a generator 2 is applied to an input 321 of a delay circuit 32 where the reference signal is delayed for a delay time τ. The delay is controlled by delay control signal, applied to input 322 of the delay circuit. Delay circuit has an output 323, connected with an input 312 of the multiplier. The response signal and delayed reference signal are multiplied in the multiplier. A multiplication product is then applied through an output 313 of a multiplier to an input 331 of low pass filter 33, where the signal is averaged so that the high frequency carrier is zeroed out and the correlation product CT,τ(t), that is changing with the impedance Ż, is extracted out. The correlation product depends not only on the impedance Ż, but also on the frequency of the excitation signal f=1/T, and the predetermined delay τ.

Characteristic measurement frequencies $f_L$ and $f_H$ for a particular object are selected so that the delay τ is short, for example shorter than $T_L/30$ (or $T_H/30$, respectively) and in another example, shorter than $T_L/36$ (or $T_H/36$, respectively). Such delay should provide the maximal value for correlation product (corresponds to about 90-95% of the maximum correlation product for inphase sine signals). If not, the measurement frequencies $f_L$ and $f_H$ should be tuned (changed/selected) so that the maximum correlation is achieved.

It may be reasonable to use some predetermined delays τ, for example $\tau_{max}=T/4$ and $\tau_{min}=0$, to get additional results at these well defined values of delays. In the case of measuring on intermediate frequencies $f_M$, the delays between 0 to T/4 can be used.

Figure 4:
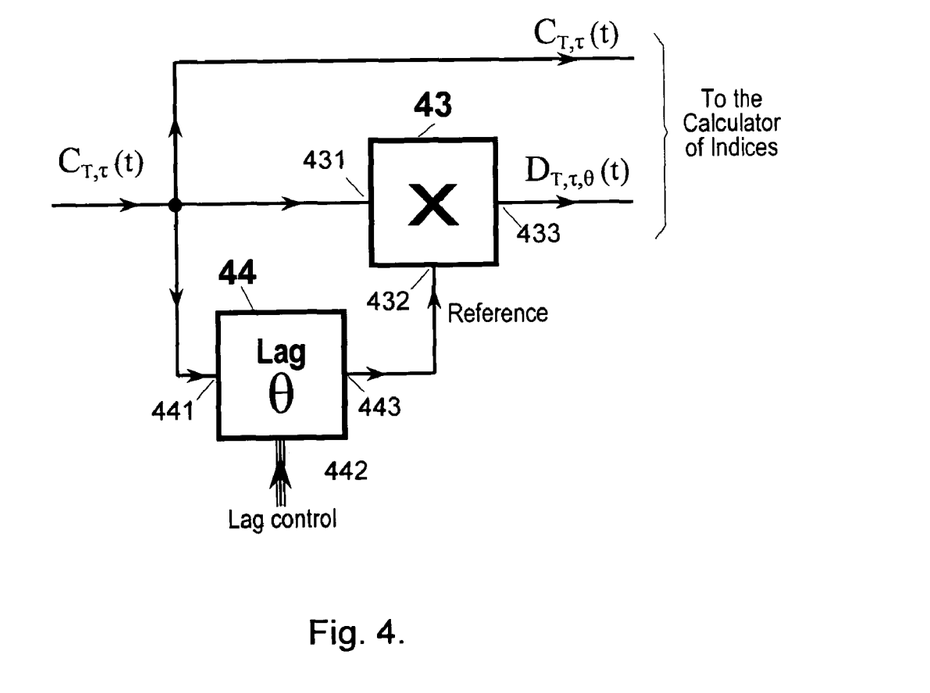
FIG. 4 is an auto-correlator of data, used in the device on FIG. 2 to correlate cross-correlation products according to one embodiment of present invention.

FIG. 4 describes the auto-correlator 41 in more details. Auto-correlator 41 comprises multiplier 43 and lag circuit 44. A signal from cross-correlator 3 is applied to an input 431 of multiplier 43 and to input 441 of lag circuit 44. Lag interval θ is controlled by lag control signal, applied to input 442 of the lag circuit 44. A reference signal with lag interval θ is applied through output 443 of the lag circuit to input 432 of the multiplier. Signals are multiplied in a multiplier and a signal at output 433 of the multiplier represents an auto-correlation product of cross-correlation products at moment t and at the earlier moment t−θ. Thus, autocorrelation provides a comparison of parameters of the tissue, measured at moment t, with parameters, measured earlier at the moment t−θ.

The cross correlation and auto-correlation products $C_{T,\tau}(t)$ and $D_{T,\tau,\theta}(t)$ are used in arithmetical unit to calculate relative edema indicia and differentials from the products calculated the lag period θ earlier for predetermined values of T and τ, for example $$\frac{C(t) \cdot C(t-\theta)}{C_0^2} \text{ or } \frac{C(t) - C(t-\theta)}{C_0}$$

and other relative values for different values of T, τ and θ, characterizing the state of tissue from different aspects, where $C_0$ is an initial value of cross-correlation.

No comparison with healthy tissue is needed according to invention, but rather the same tissue is monitored at different moments of time, at different frequencies of the excitation signal, and for different delay times and lag intervals. The results are represented digitally and/or graphically.

As the in vivo measurements are needed, a permanent physiological modulation of the impedance (biomodulation) besides the edema processes takes place in some tissues and organs (heart beating, breathing, rhythmic blood flow). Thus, a comparison of impedances measured at different frequencies is to be accomplished fully or almost simultaneously at the moments which are practically identical. For the cardiac ischemia monitoring, only the fully simultaneous measurements are trustable because the beat-to-beat changes of intracardiac impedance are typically substantially bigger than the slow changes from edema (ischemia).

Figure 5:
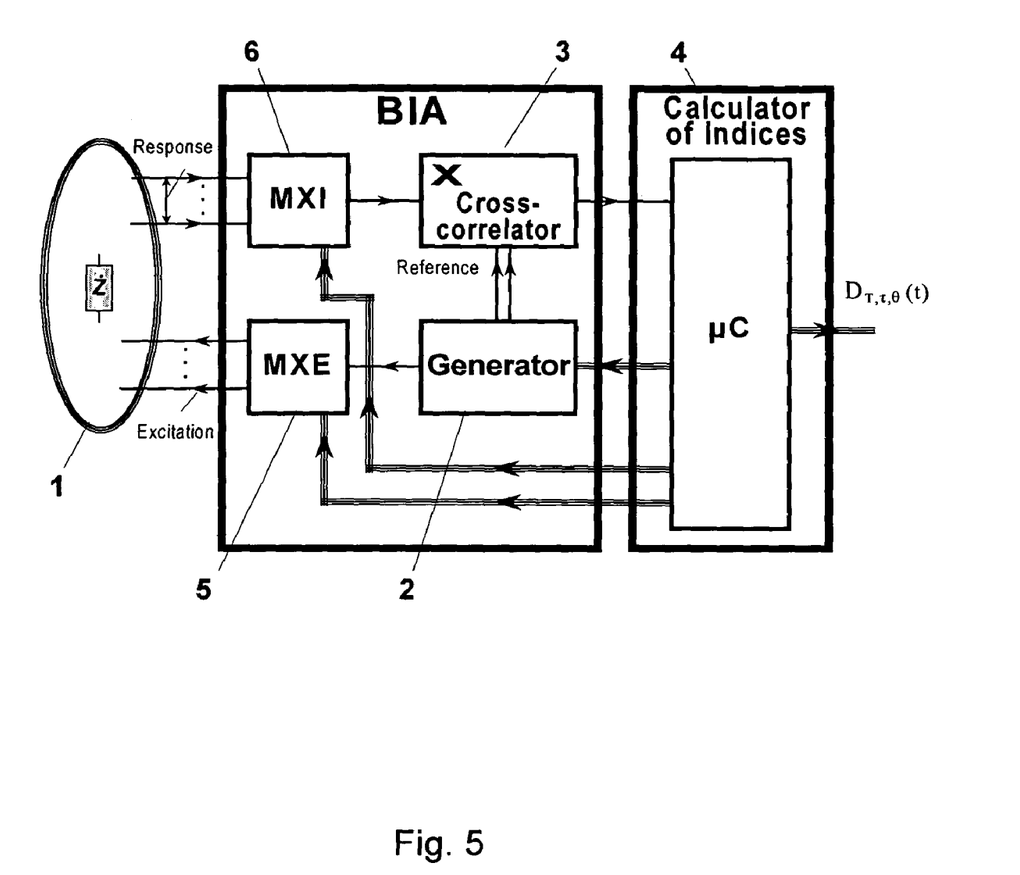
FIG. 5 is a structural scheme of an edema analyzer according to another embodiment of the invention, adopted for almost simultaneous measurements of EBI at different parts (areas, compartments) of the tissue or organ.

A bioimpedance analyser (BIA) is depicted in FIG. 5, for monitoring edema in a bio-object 1 having an impedance Ż and is adopted for simultaneous or almost simultaneous measurements at different places, parts, and compartments of the bio-object such as a tissue or organ. The edema analyzer includes generator 2 of excitation and reference signals, cross-correlator 3 and a calculator of edema indices 4, accomplished using a microcomputer μC or microcontroller. The excitation is injected into different areas of the bio-object by the aid of an excitation multiplexer (MXE) 5, and the excitation responses are leaded through an input multiplexer (MXI) 6 to cross-correlator 3. The microcontroller unit μC converts the demodulated signals into a digital code and subjects the data to digital processing to obtain and show the edema information.

Figure 6:
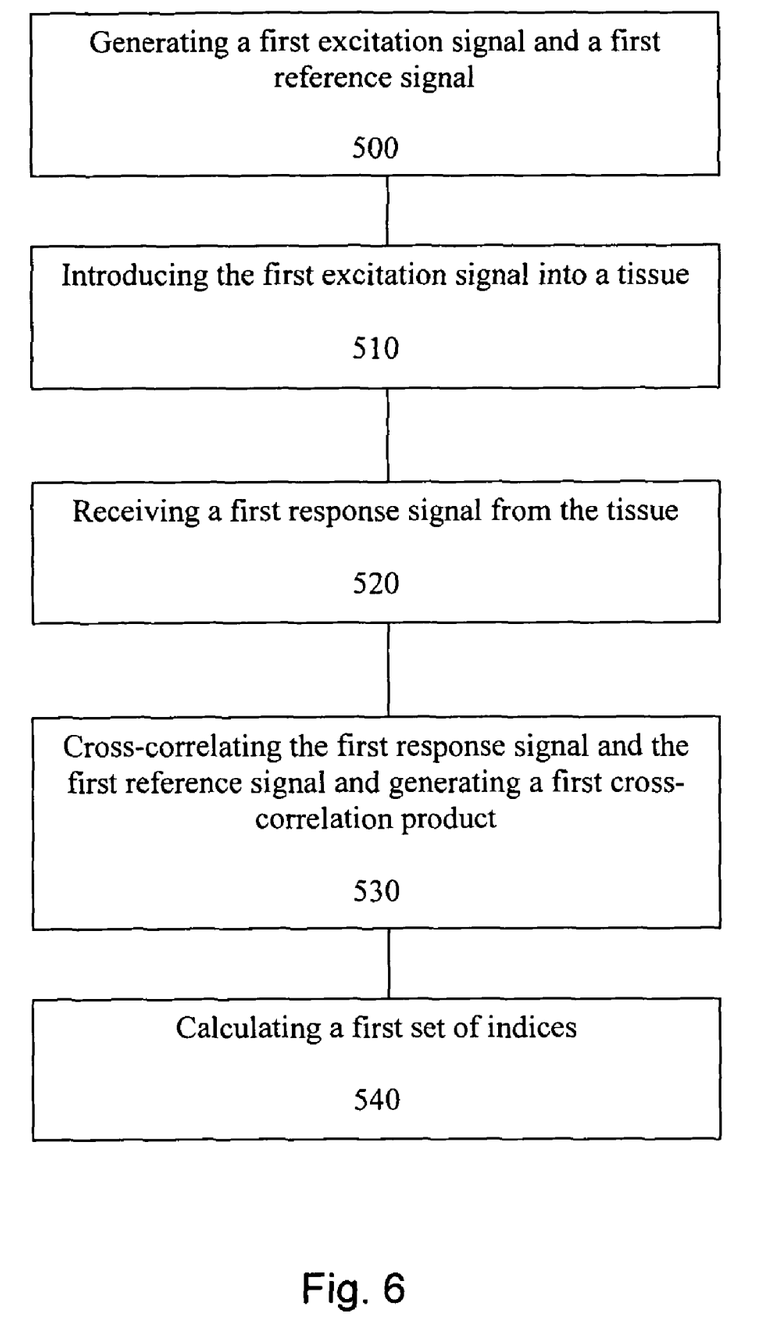
FIG. 6 is a simplified flow chart perspective according to one embodiment of present invention.

FIG. 6 illustrates the process flow according to one embodiment of the invention. The present system generates a first excitation signal having a first references signal 500. The excitation signal and the reference signal are separated by a delay as detailed herein. The system is coupled to the bio-object such as a tissue and the first excitation signal is transmitted to the bio-object 510. The system receives a first response signal from the bio-object 520 which is then processed by the system. As described herein, the first response signal and the first reference signal are cross-correlated in order to generate a first cross-correlation product 530. Additional processing calculates a first set of indices that is used to characterize the state of the bio-object.

Although this invention is described with respect to a set of aspects and embodiments, modifications thereto will be apparent to those skilled in the art. The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A method for determining conditions of a bio-object, comprising a biological tissue by measuring electrical characteristics of the bio-object, the method comprising:
generating a first excitation signal and generating a first reference signal, whereas said first reference signal is delayed compared to said first excitation signal by a first delay time and said first excitation signal having a periodic waveform with a first predetermined frequency;
introducing said first excitation signal into the bio-object and receiving a first response signal from the bio-object;
cross-correlating said first response signal and said first reference signal, thereby producing a first cross-correlation product, said first cross-correlation product being a real number; and
calculating a first set of indices characterizing conditions of the bio-object, based on said first cross-correlation product and said first delay time, wherein said first delay time is selected so as to maximize said first cross-correlation product for said first predetermined frequency.

2. A method as in claim 1, wherein said first excitation signal is a sine wave and said first predetermined frequency is selected low enough so that a current caused by said first excitation signal flows mostly through an extracellular liquid of the biological tissue and said first cross-correlation product corresponding to said first excitation signal reflects the amount of extracellular liquid in the biological tissue.

3. A method according to claim 2, wherein the first predetermined frequency is between about 10 to about 1000 Hz and is chosen so that the maximal value of said cross-correlation product is obtained at said first delay time being less than about $1/30$ of the period of said first excitation signal.

4. A method as in claim 1, wherein said first excitation signal is a sine wave and said first predetermined frequency that is selected so that a current caused by said first excitation signal is capable to flow through cell membranes of the biological tissue so that said first cross-correlation product corresponding to said first excitation signal reflects the total amount of liquid in intracellular and extracellular region of the biological tissue.

5. A method according to claim 4, wherein the first predetermined frequency is between about approximately 10 kHz to about approximately 10 MHz and is chosen so that the maximal value of said first cross-correlation product is obtained at said first delay time being less than about approximately $1/30$ of the period of said first excitation signal.

6. A method as in claim 1, additionally comprising generating a second excitation signal and a second reference signal, wherein said second reference signal is delayed compared to said second excitation signal by a second delay time, and introducing said second excitation signal into the biological tissue and receiving a second response signal from the biological tissue, cross-correlating said second response signal and said second reference signal, thereby producing a second cross-correlation product, and calculating a second set of indices to describe the condition of the biological tissue, based on said second cross-correlation product and said second delay time.

7. A method as in claim 6, wherein said first excitation signal is a first periodic sine wave and said first predetermined frequency and said second excitation signal is a periodic sine wave with a second predetermined frequency, wherein said first predetermined frequency is selected so that said first excitation signal flows mostly through an extracellular liquid of the biological tissue and said first cross-correlation product corresponding to said first excitation signal reflects the amount of extracellular liquid in the biological tissue and said second predetermined frequency is selected so that said second excitation signal is capable to flow through cell membranes of the biological tissue so that said second cross-correlation product corresponding to said second excitation signal reflects the total amount of liquid in the intracellular and the extracellular region of the biological tissue.

8. A method as in claim 7, wherein said first predetermined frequency is between about 10 to about 1000 Hz and said second predetermined frequency is about 10 kHz to about approximately 10 MHz, whereas said second predetermined frequency are selected so as to maximize said first cross-correlation product and said second cross-correlation product and at said first delay time and said second delay time being less than about $1/30$ of a period of said first excitation signal and said second excitation signal respectively.

9. A method as in claim 7, additionally comprising generating a third excitation signal and a third reference signal, whereas said third reference signal is delayed compared to said third excitation signal by a third delay time, and introducing said third excitation signal into the biological tissue and receiving a third response signal from the biological tissue, cross-correlating said third response signal and said third reference signal, thereby producing a third cross-correlation product, and calculating a third set of indices to describe the condition of the biological tissue, based on said third cross-correlation product and said third delay time, and wherein said third reference signal is a third sine wave with a third predetermined frequency, said third predetermined frequency being higher than said first predetermined frequency and lower than said second predetermined frequency, and wherein said third delay time between said third excitation signal and said third reference signal is adjusted to a value between about approximately $1/30$ and $1/4$ of a period of said third excitation signal to maximize the value of the third cross-correlation product.

10. A method as in claim 6, wherein said first excitation signal is a first periodic sine wave and said second excitation signal is a second periodic sine wave with a second predetermined frequency, whereas both said first excitation signal and said second excitation signal are introduced simultaneously into the biological tissue.

11. A method as in claim 9, wherein said first excitation signal, said second excitation signal and said third excitation signal are introduced simultaneously into the biological tissue.

12. A method as in claim 6, wherein said first excitation signal is a first periodic sine wave and said second excitation signal is a second periodic sine wave with a second predetermined frequency, whereas said first excitation signal and said second excitation signal are introduced into the biological tissue in turns at different time intervals and corresponding said first cross-correlation products and said second cross-correlation products are produced for different moments of time which correspond to said different time intervals.

13. A method as in claim 9, wherein said first excitation signal, said second excitation signal and said third excitation signal are introduced into the biological tissue in turns at different time intervals and corresponding said first cross-correlation products, said second cross-correlation products and said third cross-correlation products are produced for different moments of time which correspond to said different time intervals.

14. A method according to claim 1, wherein said first excitation signal consists of pulse waves.

15. A method according to claim 14, wherein the said pulse waves are trains of rectangular pulses with predetermined duty-cycle and pulse widths.

16. A method according to claim 6, wherein at least one of said first excitation signal and said second excitation signal consists of pulse waves.

17. A method for determining conditions of a bio-object, comprising a biological tissue, by measuring electrical characteristics of the bio-object, the method comprising:

generating a periodic sine wave excitation signal and generating a reference signal corresponding to said excitation signal, whereas said reference signal is delayed compared to said excitation signal by a delay time;

introducing said excitation signal into the bio-object and receiving a response signal from the bio-object;

cross-correlating said response signal and said reference signal at different moments of time, thereby producing a set of non-complex cross-correlation products, characterizing the state of the bio-object at different moments of time; said delay time being selected so as to maximize said non-complex cross-correlation products auto-correlating said non-complex cross-correlation products at different lag intervals to produce auto-correlation products; and calculating a set of indices from said auto-correlation products corresponding to the changes in said state of the bio-object.

18. A method according to claim 17, wherein said set of indices is selected from the group consisting of revivability of a transplanted tissue, and reperfusion and resuscitation processes in a transplanted tissue.

* * * * *